United States Patent
Tanaka et al.

(10) Patent No.: US 10,780,107 B2
(45) Date of Patent: Sep. 22, 2020

(54) AGENT FOR INDUCING CELL DEATH, AGENT FOR SUPPRESSING CELL PROLIFERATION, AND PHARMACEUTICAL COMPOSITION USED FOR TREATMENT OF DISEASE RESULTING FROM ABNORMAL CELL PROLIFERATION

(71) Applicant: Nitto Denko Corporation, Osaka (JP)

(72) Inventors: Hiroyuki Tanaka, Osaka (JP); Kenjirou Minomi, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 16/310,795

(22) PCT Filed: Jun. 23, 2017

(86) PCT No.: PCT/JP2017/023121
§ 371 (c)(1),
(2) Date: Dec. 17, 2018

(87) PCT Pub. No.: WO2017/222035
PCT Pub. Date: Dec. 28, 2017

(65) Prior Publication Data
US 2019/0151344 A1    May 23, 2019

(30) Foreign Application Priority Data
Jun. 23, 2016  (JP) .................. 2016-124252

(51) Int. Cl.
*A61K 48/00* (2006.01)
*C07H 21/04* (2006.01)
*A61K 31/7088* (2006.01)
*A61P 35/00* (2006.01)
*A61K 45/06* (2006.01)
*A61K 45/00* (2006.01)
*A61P 43/00* (2006.01)
*A61K 31/713* (2006.01)
*A61K 31/7105* (2006.01)
*C12Q 1/02* (2006.01)

(52) U.S. Cl.
CPC ........ *A61K 31/7088* (2013.01); *A61K 31/713* (2013.01); *A61K 31/7105* (2013.01); *A61K 45/00* (2013.01); *A61K 45/06* (2013.01); *A61K 48/00* (2013.01); *A61P 35/00* (2018.01); *A61P 43/00* (2018.01); *C12Q 1/025* (2013.01)

(58) Field of Classification Search
CPC .. C12N 15/113; C12N 2310/11; A61K 31/713
See application file for complete search history.

(56) References Cited

U.S. PATENT DOCUMENTS 9,151,758 B2 * 10/2015 Zetter .................. G01N 33/574
9,914,983 B2    3/2018 Niitsu et al.
2007/0099209 A1 * 5/2007 Clarke ................. C12Q 1/6886
435/6.12
2011/0236903 A1    9/2011 McClelland et al.
2013/0028885 A1    1/2013 Zetter et al.
2014/0011861 A1 * 1/2014 McClelland ......... C12Q 1/6886
514/44 A
2014/0315975 A1   10/2014 Niitsu et al.
2015/0328248 A1   11/2015 Niitsu
2017/0137825 A1    5/2017 Niitsu

FOREIGN PATENT DOCUMENTS

| CN | 102308212 A | 1/2012 |
| CN | 103619355 A | 3/2014 |
| CN | 104884090 A | 9/2015 |
| EP | 2724729 A1 | 4/2014 |
| EP | 2937099 A1 | 10/2015 |
| JP | 2002510490 A | 4/2002 |
| WO | 1999051741 | 10/1999 |
| WO | 2012176282 A1 | 12/2012 |
| WO | 2014098210 A1 | 6/2014 |
| WO | 2015194522 A1 | 12/2015 |

OTHER PUBLICATIONS

Elbashir et al. (The EMBO Journal, vol. 20, No. 23, pp. 6877-6888, 2001).*
International Search Report and Written Opinion dated Aug. 8, 2017 in corresponding PCT/JP2017/023121 in 7 pages.
International Preliminary Report on Patentability dated Dec. 25, 2018 in corresponding PCT/JP2017/023121 in 7 pages.
Futreal, A Census of Human Cancer Genes, 2004, Nat Rev Cancer, vol. 4(3), pp. 177-183.
Takahashi, 1994, Gan to Kagaku Ryoho, vol. 21(7), pp. 945-951 (concise English explanation).
Takahashi, 1994, Gan to Kagaku Ryoho, vol. 21(7), pp. 945-951.
Ban, Transfection of Glutathione S-Transferase (GST)-Pi Antisense Complementary DNA Increases the Sensitivity of a Colon Cancer Cell Line to Adriamycin, Cisplatin, Melphalan, and Etoposide, 1996, Cancer Research, vol. 56, pp. 3577-3582.
Nakajima, Reversal of Multiple Drug Resistance in Cholangiocarcinoma by the Glutathione S-Transferase-Pi-Specific Inhibitor O1-Hexadecyl-gamma-glutamyl-S-benzylcysteinyl-D-phenylglycine Ethylester, 2003, Journal of Pharmacology and Experimental Therapeutics, vol. 306, pp. 861-869.
Hokaiwado, Glutathione S-transferase Pi mediates proliferation of androgen-independent prostate cancer cells, 2008, Carcinogenesis, vol. 29, pp. 1134-1138.
Adler, Regulation of JNK signaling by GSTp, 1999, The EMBO Journal, vol. 18, pp. 1321-1334.

(Continued)

*Primary Examiner* — Amy H Bowman
(74) *Attorney, Agent, or Firm* — Knobbe, Martens, Olson & Bear LLP

(57) ABSTRACT

This invention provides an agent and a composition that induces cancer cell death and suppresses cancer cell proliferation. The agent and the composition comprises, as an active ingredient, a drug for suppressing GST-$\pi$ and MRPL17 or comprises, as active ingredients, a drug for suppressing GST-$\pi$ and a drug for suppressing MRPL17.

13 Claims, 1 Drawing Sheet

Specification includes a Sequence Listing.

(56) References Cited

OTHER PUBLICATIONS

Townsend, Novel Role for Glutathione S-Transferase Pi, 2009, Journal of Biological Chemistry, vol. 284 pp. 436-445.
Yin, Glutathione S-Transferase p Elicits Protection against H2O2-induced Cell Death via Coordinated Regulation of Stress Kinases, 2000, Cancer Research, vol. 60, pp. 4053-4057.
Nishita, Regulation of autophagy and MAPK signaling by glutathione S-transferase-Pi in KRAS mutated cancer cells, #1065, 2011, Proceedings of the American Association for Cancer Research, vol. 52, pp. 257.
Office Action issued in CA patent application No. 3028934, dated Oct. 23, 2019.
De Luca et al., "Glutathione S-transferase Pi-1 as a target for mesothelioma treatment", Cancer Science, vol. 104, No. 2, Feb. 1, 2013.
McKee et al., "Inhibition of mammalian mitochondrial protein synthesis by oxazolidinones", Antimicrobial Agents and Chemotherapy, American Society for Microbiology, US vol. 50, No. 6, Jun. 1, 2006.
Nagiec et al., "Oxazolidinones inhibit cellular proliferation via inhibition of mitochondrial protein synthesis", Antimicrobial Agents and Chemotherapy, American Society for Microbiology, US, vol. 49, No. 9, Sep. 1, 2005.
Naresh et al., "Oxazolidinone derivatives: Cytoxazone-Linezolid hybrids induces apoptosis and senescence in DU145 prostate cancer cells", European Journal of Medicinal Chemistry, vol. 80, Jun. 1, 2014.
Supplementary Search Report issued in EP application No. 17815500. 8, dated Feb. 11, 2020.
Office Action of Chinese Application No. 201780037368.7 dated Jun. 30, 2020.

* cited by examiner

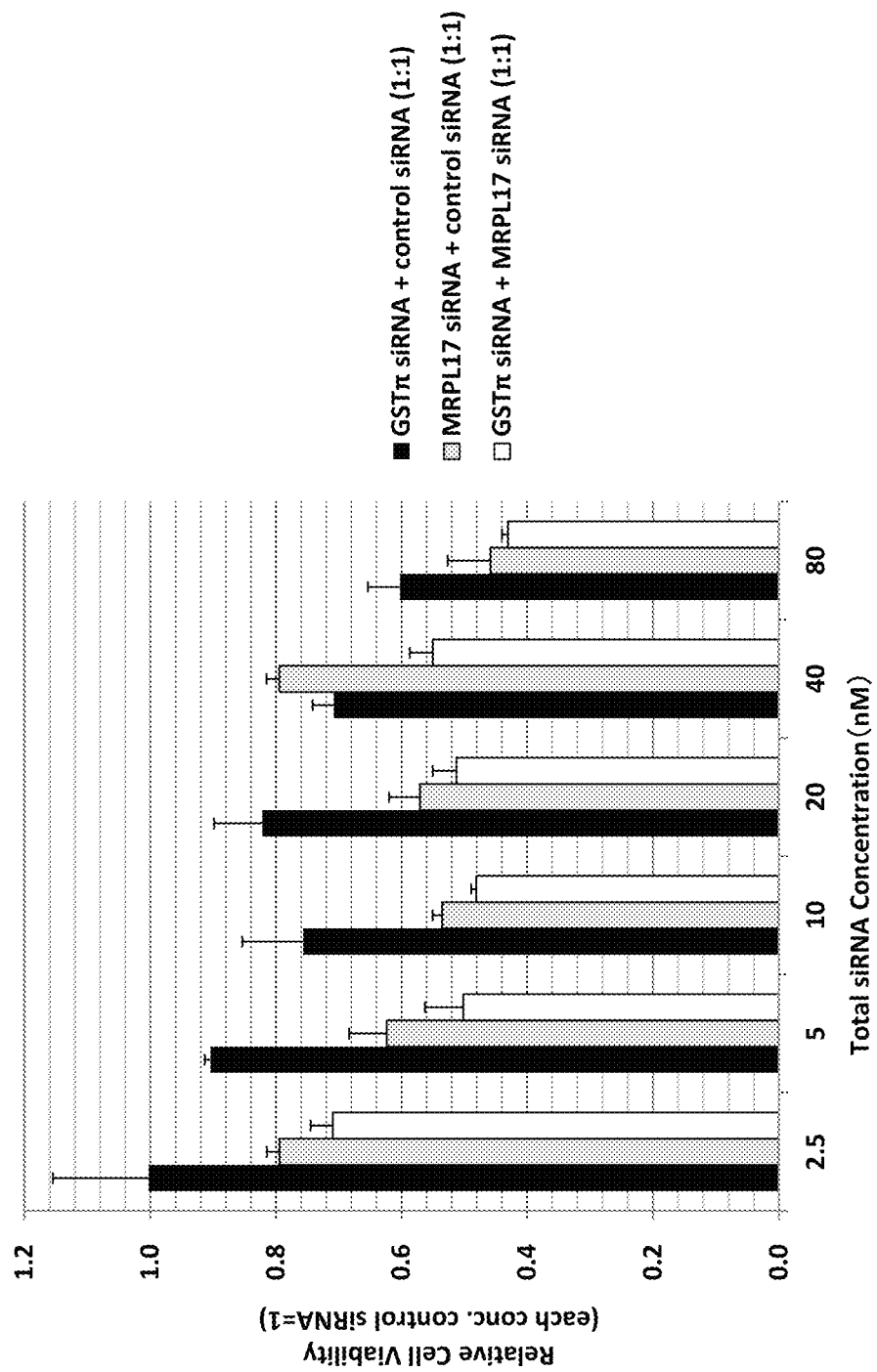

SEQUENCE LISTING

```
<160> NUMBER OF SEQ ID NOS: 10

<210> SEQ ID NO 1
<211> LENGTH: 986
<212> TYPE: DNA
<213> ORGANISM: Homo sapiens
<220> FEATURE:
<221> NAME/KEY: CDS
<222> LOCATION: (250)..(882)

<400> SEQUENCE: 1
tgggaaagag ggaaaggctt ccccggccag ctgcgcggcg actccgggga ctccagggcg        60 ccctctgcg gccgacgccc ggggtgcagc ggccgccggg gctggggccg gcgggagtcc        120
gcgggaccct ccagaagagc ggccggcgcc gtgactcagc actggggcgg agcggggcgg        180
gaccacccct ataaggctcg gaggccgcga ggccttcgct ggagtttcgc cgccgcagtc        240 ttcgccacc atg ccg ccc tac acc gtg gtc tat ttc cca gtt cga ggc cgc        291
          Met Pro Pro Tyr Thr Val Val Tyr Phe Pro Val Arg Gly Arg
           1               5                  10 tgc gcg gcc ctg cgc atg ctg ctg gca gat cag ggc cag agc tgg aag        339
Cys Ala Ala Leu Arg Met Leu Leu Ala Asp Gln Gly Gln Ser Trp Lys
15                  20                  25                  30 gag gag gtg gtg acc gtg gag acg tgg cag gag ggc tca ctc aaa gcc        387
Glu Glu Val Val Thr Val Glu Thr Trp Gln Glu Gly Ser Leu Lys Ala
                35                  40                  45 tcc tgc cta tac ggg cag ctc ccc aag ttc cag gac gga gac ctc acc        435
Ser Cys Leu Tyr Gly Gln Leu Pro Lys Phe Gln Asp Gly Asp Leu Thr
            50                  55                  60 ctg tac cag tcc aat acc atc ctg cgt cac ctg ggc cgc acc ctt ggg        483
Leu Tyr Gln Ser Asn Thr Ile Leu Arg His Leu Gly Arg Thr Leu Gly
65                  70                  75 ctc tat ggg aag gac cag cag gag gca gcc ctg gtg gac atg gtg aat        531
Leu Tyr Gly Lys Asp Gln Gln Glu Ala Ala Leu Val Asp Met Val Asn
        80                  85                  90 gac ggc gtg gag gac ctc cgc tgc aaa tac atc tcc ctc atc tac acc        579
Asp Gly Val Glu Asp Leu Arg Cys Lys Tyr Ile Ser Leu Ile Tyr Thr
95                  100                 105                 110 aac tat gag gcg ggc aag gat gac tat gtg aag gca ctg ccc ggg caa        627
Asn Tyr Glu Ala Gly Lys Asp Asp Tyr Val Lys Ala Leu Pro Gly Gln
                115                 120                 125 ctg aag cct ttt gag acc ctg ctg tcc cag aac cag gga ggc aag acc        675
Leu Lys Pro Phe Glu Thr Leu Leu Ser Gln Asn Gln Gly Gly Lys Thr
            130                 135                 140 ttc att gtg gga gac cag atc tcc ttc gct gac tac aac ctg ctg gac        723
Phe Ile Val Gly Asp Gln Ile Ser Phe Ala Asp Tyr Asn Leu Leu Asp
        145                 150                 155 ttg ctg ctg atc cat gag gtc cta gcc cct ggc tgc ctg gat gcg ttc        771
Leu Leu Leu Ile His Glu Val Leu Ala Pro Gly Cys Leu Asp Ala Phe
    160                 165                 170 ccc ctg ctc tca gca tat gtg ggg cgc ctc agt gcc cgg ccc aag ctc        819
Pro Leu Leu Ser Ala Tyr Val Gly Arg Leu Ser Ala Arg Pro Lys Leu
```

```
                175                 180                 185                 190
aag gcc ttc ctg gcc tcc cct gag tac gtg aac ctc ccc atc aat ggc      867
Lys Ala Phe Leu Ala Ser Pro Glu Tyr Val Asn Leu Pro Ile Asn Gly
            195                 200                 205 aac ggg aaa cag tga gggttggggg gactctgagc gggaggcaga gtttgccttc      922
Asn Gly Lys Gln
        210 ctttctccag gaccaataaa atttctaaga gagctaaaaa aaaaaaaaaa aaaaaaaaa     982 aaaa                                                                 986

<210> SEQ ID NO 2
<211> LENGTH: 210
<212> TYPE: PRT
<213> ORGANISM: Homo sapiens

<400> SEQUENCE: 2

Met Pro Pro Tyr Thr Val Val Tyr Phe Pro Val Arg Gly Arg Cys Ala
1               5                   10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Ile Ser Leu Ile Tyr Thr Asn Tyr
            100                 105                 110

Glu Ala Gly Lys Asp Asp Tyr Val Lys Ala Leu Pro Gly Gln Leu Lys
        115                 120                 125

Pro Phe Glu Thr Leu Leu Ser Gln Asn Gln Gly Gly Lys Thr Phe Ile
    130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190

Phe Leu Ala Ser Pro Glu Tyr Val Asn Leu Pro Ile Asn Gly Asn Gly
        195                 200                 205

Lys Gln
    210

<210> SEQ ID NO 3
<211> LENGTH: 2366
<212> TYPE: DNA
<213> ORGANISM: Homo sapiens
<220> FEATURE:
<221> NAME/KEY: CDS
<222> LOCATION: (106)..(633)

<400> SEQUENCE: 3
accacgctcc gagctaaggc gcatgcgttc cctgaaattg ccgccaccgg ctctaccttc      60
cagtttccag ttccggcctc caaggggcgg gcagaagttg gaaac atg cgg ctg tcg     117
                                                 Met Arg Leu Ser
```

```
                                                                  -continued
                                                         1 gtc gct gca gcg atc tcc cat ggc cgc gta ttt cgc cgt atg ggc ctc      165
Val Ala Ala Ala Ile Ser His Gly Arg Val Phe Arg Arg Met Gly Leu
 5              10                  15                  20 ggt ccc gag tcc cgc atc cat ctg ttg cgg aac ttg ctc aca ggg ctg      213
Gly Pro Glu Ser Arg Ile His Leu Leu Arg Asn Leu Leu Thr Gly Leu
                25                  30                  35 gtg cgg cac gaa cgc atc gag gca cca tgg gcg cgt gtg gac gaa atg      261
Val Arg His Glu Arg Ile Glu Ala Pro Trp Ala Arg Val Asp Glu Met
            40                  45                  50 agg ggc tac gcg gag aag ctc atc gac tat ggg aag ctg gga gac act      309
Arg Gly Tyr Ala Glu Lys Leu Ile Asp Tyr Gly Lys Leu Gly Asp Thr
        55                  60                  65 aac gaa cga gcc atg cgc atg gct gac ttc tgg ctc aca gag aag gat      357
Asn Glu Arg Ala Met Arg Met Ala Asp Phe Trp Leu Thr Glu Lys Asp
    70                  75                  80 ttg atc cca aag ctg ttt caa gta ctg gcc cct cgg tac aaa gat caa      405
Leu Ile Pro Lys Leu Phe Gln Val Leu Ala Pro Arg Tyr Lys Asp Gln
85                  90                  95                 100 act ggg ggc tac aca aga atg ctg cag atc cca aat cgg agt ttg gat      453
Thr Gly Gly Tyr Thr Arg Met Leu Gln Ile Pro Asn Arg Ser Leu Asp
                105                 110                 115 cgg gcc aag atg gca gtg atc gag tat aaa ggg aat tgc ctc cca ccc      501
Arg Ala Lys Met Ala Val Ile Glu Tyr Lys Gly Asn Cys Leu Pro Pro
            120                 125                 130 ctg cct ctg cct cgc aga gac agc cac ctt aca ctc cta aac cag ctg      549
Leu Pro Leu Pro Arg Arg Asp Ser His Leu Thr Leu Leu Asn Gln Leu
        135                 140                 145 ctg cag ggt ttg cgg cag gac ctc agg caa agc cag gaa gca agc aac      597
Leu Gln Gly Leu Arg Gln Asp Leu Arg Gln Ser Gln Glu Ala Ser Asn
    150                 155                 160 cac agc tcc cac aca gct caa aca cca ggg att taa ctggatctga          643
His Ser Ser His Thr Ala Gln Thr Pro Gly Ile
165                 170                 175 agagtctgca gcccttaatc agtacccatg atcacaggcc tttggagcac ttttactctc    703
tgagaagaac tggagctaga gatgtaaaat ggacagtctt gatggggttg agaaccttct    763
ggggagccag atgaccctct ctttgcacaa tagataaaag tctttatatg aatatatata    823
aatttattta ttttttcctt cctgtgggat ttctggagaa tgagaattat ccaaatgctc    883
agtctacctg agatagtaaa ttcatggctt atgcttctgg tccttaaatt tgggttattt    943
ttggttagtg caattttgtt tttcttaatg ccagtttaca tgggaatgca tcctataatt   1003
ccaaatgttg ccagaggtgg ttgtgttttg acatctggtc tcctagagat gagtgcttgg   1063
gatttcttag agaaagatta cttcctgaca ggggtagggg agtgacaatc tgcaagtgaa   1123
acttccttaa acaatctagt accctgcgaa ccttcagggg atactgcaat cagtcctctg   1183
ttttgaggca ggatcacaca ttaccttaat gtgttccctt caaccccctg aatgggcctg   1243
ggaggagagg acccaagaac tcagatgttc caccagtttg ccaaagggg tggagacatt    1303
cagcagagga tgttgggctc caggataagc tccttcctct tggtgagggg aaggggtaag   1363
aaagagggtc tatgcgagag aaggattagg aaattaaacc tcctaggaat ttcctggaag   1423
tttttattgt tgtcaaatct ggcctctctg ggaacccaga aaagggaaat ccggcttcag   1483
aatgtgagaa gctgggagcc cctttcttgg cacagccagg ctgccgttcc cttgggttca   1543
gaggctttag tagggtagta gttatggaag gacttagaaa ggagccatca gtcttggtcc   1603
aaacacttga tagcagtgcc tgataattgc catatcccca gtaaagtggg tagaagagat   1663
```

```
tttatcttag gctctatctt ctgagtgtat ttggcccact gaacccatcc actgtctgag    1723
ataataagta agagtaaggg taaagggatc actggtgtag cagacatggc ttcagtgaca    1783
gaacgaacta ttctggtgct aatttagctg tagctgcctt agtctgatac tcatctactc    1843
ccaacagagc tctttatctc ttttttctcta ctatggtttg ttcttcacac tatagccaga   1903
aagctcttat attttaaatg aaatatagta gacactcaaa acatttatga aataaagcta    1963
caactctgct tctgctaaaa aatataccc tcttctgtct tagcatgaat atccaccta      2023 gctaggtatc taggagtcat acctaacttc tagagaaacc actttcctta aaaccacatc    2083
tttattttaa atagatggat tgtggctggg ctcctgtagc ttttcctctt agaccccaga    2143
aatatatctc cctttgggac ttccaacagt tccctacatg cttttttgagc atctgctagt   2203 tcccagcatc aatttaggca aagggatac aatatccact gttcatctaa tagagactag     2263
agataagaaa caacctgtac catcaatgag ctcacaataa caggccactg ccactaccac    2323
agtggcctca agggacactg cttcccttt aatgttttgg tcc                       2366
```

<210> SEQ ID NO 4
<211> LENGTH: 175
<212> TYPE: PRT
<213> ORGANISM: Homo sapiens

<400> SEQUENCE: 4

```
Met Arg Leu Ser Val Ala Ala Ile Ser His Gly Arg Val Phe Arg
1               5                   10                  15

Arg Met Gly Leu Gly Pro Glu Ser Arg Ile His Leu Leu Arg Asn Leu
            20                  25                  30

Leu Thr Gly Leu Val Arg His Glu Arg Ile Glu Ala Pro Trp Ala Arg
        35                  40                  45

Val Asp Glu Met Arg Gly Tyr Ala Glu Lys Leu Ile Asp Tyr Gly Lys
    50                  55                  60

Leu Gly Asp Thr Asn Glu Arg Ala Met Arg Met Ala Asp Phe Trp Leu
65                  70                  75                  80

Thr Glu Lys Asp Leu Ile Pro Lys Leu Phe Gln Val Leu Ala Pro Arg
                85                  90                  95

Tyr Lys Asp Gln Thr Gly Gly Tyr Thr Arg Met Leu Gln Ile Pro Asn
            100                 105                 110

Arg Ser Leu Asp Arg Ala Lys Met Ala Val Ile Glu Tyr Lys Gly Asn
        115                 120                 125

Cys Leu Pro Pro Leu Pro Leu Pro Arg Arg Asp Ser His Leu Thr Leu
    130                 135                 140

Leu Asn Gln Leu Leu Gln Gly Leu Arg Gln Asp Leu Arg Gln Ser Gln
145                 150                 155                 160

Glu Ala Ser Asn His Ser Ser His Thr Ala Gln Thr Pro Gly Ile
                165                 170                 175
```

<210> SEQ ID NO 5
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA

```
<400> SEQUENCE: 5
ccuuuugaga cccugcugut t                                         21

<210> SEQ ID NO 6
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA

<400> SEQUENCE: 6
acagcagggu cucaaaaggc t                                         21

<210> SEQ ID NO 7
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA

<400> SEQUENCE: 7
uggcagugau cgaguauaat t                                         21

<210> SEQ ID NO 8
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA

<400> SEQUENCE: 8
uuauacucga ucacugccat t                                         21

<210> SEQ ID NO 9
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA

<400> SEQUENCE: 9
acgugacacg uucggagaat t                                         21

<210> SEQ ID NO 10
<211> LENGTH: 21
<212> TYPE: DNA
<213> ORGANISM: Artificial
<220> FEATURE:
<223> OTHER INFORMATION: Combined DNA/RNA molecule: Synthetic
```

```
        oligonucleotide
<220> FEATURE:
<221> NAME/KEY: misc_feature
<222> LOCATION: (1)..(19)
<223> OTHER INFORMATION: RNA

<400> SEQUENCE: 10
uucuccgaac gugucacgut t                                              21
```

AGENT FOR INDUCING CELL DEATH, AGENT FOR SUPPRESSING CELL PROLIFERATION, AND PHARMACEUTICAL COMPOSITION USED FOR TREATMENT OF DISEASE RESULTING FROM ABNORMAL CELL PROLIFERATION

TECHNICAL FIELD

The present invention relates to an agent for inducing cancer cell death, an agent for suppressing cancer cell proliferation, and a pharmaceutical composition used for treatment of a disease resulting from abnormal cell proliferation. The present invention further relates to a method of screening for an agent for inducing cell death and/or an agent for suppressing cell proliferation.

BACKGROUND ART

A typical example of a disease resulting from abnormal cell proliferation is cancer. Cancer is a disease resulting from uncontrolled cell proliferation caused by, for example, a gene mutation or epigenetic abnormality. Many gene abnormalities in cancer have already been reported (e.g., Non-Patent Document 1), and many of such gene abnormalities are considered to be associated with signal transduction concerning cell proliferation, differentiation, and survival. Such gene abnormalities lead to abnormalities of signal transduction in cells composed of normal molecules, a particular signal cascade is activated or inactivated, and abnormal cell proliferation is caused in the end.

While treatments for early-stage cancer were focused on suppression of cell proliferation, such treatments also suppress proliferation of physiologically normal cells, disadvantageously. Accordingly, such treatments involved side effects, such as hair loss, digestive system damage, and myelosuppression. In order to suppress such side effects, development of agents for cancer treatments based on a novel idea such as molecular-targeting agents that target gene abnormalities, abnormalities in signal transduction, and the like peculiar to cancer has been in progress.

Cancer is considered to be caused by accumulation of various abnormalities such as cancer genes, cancer suppressor cells, and DNA repair enzyme genes in the same cells. Examples of known cancer genes include RAS genes, FOS genes, MYC genes, and BCL-2 genes. Among gene abnormalities peculiar to cancer, KRAS gene mutation is observed at high frequency in many cancer species, such as about 95% of pancreatic cancer, about 45% of colon cancer, and the like. The KRAS protein is a G protein localized inside the cell membrane. A cascade such that RAS such as KRAS activates RAF such as C-RAF or B-RAF, RAF activates MEK, and MEK then activates MAPK is formed. When a point mutation occurs in KRAS, GTPase activity is lowered, a GTP-coupled active form is maintained, and signals directed toward the downstream are continuously maintained. As a result, abnormal cell proliferation takes place. As represented by the KRAS gene, cancer genes cause abnormal cell proliferation, cellular canceration takes place, and cancer develops as a disease.

Glutathione-S-transferase (GST), which is an enzyme that catalyzes glutathione conjugation, is known to allow a substance such as a drug to conjugate to glutathione (GSH) to convert the resultant into a water-soluble substance. GST is classified into 6 types of isozymes based on the amino acid sequence, and representative examples thereof include α, μ, ω, π, θ, and ζ isozymes. In particular, expression of GST-π (glutathione-S-transferase pi, which is also referred to as "GSTP1") is increased in various types of cancer cells, and it may cause resistance to some anticancer agents. When antisense DNA against GST-π or a GST-π inhibitor is allowed to act against cancer cell lines overexpressing GST-π and exhibiting drug resistance, in fact, it is known that drug resistance is suppressed (Non-Patent Documents 2 to 4). In addition, it was recently reported that, when siRNA against GST-π is allowed to act against GST-π-overexpressing androgen-independent prostate cancer cell lines, proliferation thereof is suppressed, and apoptosis is then increased (Non-Patent Document 5).

GST-π is also known to form a complex with c-Jun N-terminal kinase (JNK) and inhibit JNK activity (Non-Patent Document 6). In addition, GST-π is known to be involved in conversion of a protein associated with cellular stress responses into S-glutathione (Non-Patent Document 7). In addition, GST-π is known to contribute to protection against cell death induced by active oxygen species (ROS) (Non-Patent Document 8). Among various types of GSTs, GST-π is understood as having various features and functions.

When siRNA against GST-π is allowed to act against a cancer cell line having KRAS mutation, Akt activation is suppressed, and autophagy increases; however, induction of apoptosis is moderate (Non-Patent Document 9). Patent Document 1 discloses that cancer cell apoptosis can be induced with the use of a drug for suppressing GST-π and an autophagy inhibitor, such as 3-methyladenine, as active ingredients. In addition, Patent Document 2 discloses that simultaneous inhibition of expression of GST-π, Akt, and the like would suppress cell proliferation, cell death would be induced, and autophagy induced via inhibition of GST-π expression would be significantly suppressed via simultaneous inhibition of expression of Akt and the like.

However, the correlation between GST-π expression and cell proliferation or cell death, the role of GST-π associated with signal transduction, and other features in cancer cells have not yet been sufficiently elucidated.

PRIOR ART DOCUMENTS

Patent Documents

Patent Document 1: WO 2012/176282
Patent Document 2: WO 2014/098210
Non-Patent Documents
Non-Patent Document 1: Futreal et al., Nat. Rev. Cancer, 2004; 4 (3): 177-83
Non-Patent Document 2: Takahashi and Niitsu, Gan To Kagaku Ryoho, 1994; 21 (7): 945-51
Non-Patent Document 3: Ban et al., Cancer Res., 1996; 56 (15): 3577-82
Non-Patent Document 4: Nakajima et al., J. Pharmacol. Exp. Ther., 2003; 306 (3): 861-9
Non-Patent Document 5: Hokaiwado et al., Carcinogenesis, 2008; 29 (6): 1134-8
Non-Patent Document 6: Adler et. al, EMBO J., 1999, 18, 1321-1334
Non-Patent Document 7: Townsend, et. al, J. Biol. Chem., 2009, 284, 436-445
Non-Patent Document 8: Yin et. al, Cancer Res., 2000 60, 4053-4057
Non-Patent Document 9: Nishita et al., AACR 102nd Annual Meeting, Abstract, No. 1065

SUMMARY OF THE INVENTION

Objects to Be Attained by the Invention

It is an object of the present invention to provide an agent having effects of inducing cell death and/or inhibiting cell proliferation on cancer cells, it is another object to provide a pharmaceutical composition used for treatment of a disease resulting from abnormal cell proliferation, and it is a further object to provide a method for screening for an agent for inducing cell death and/or an agent for suppressing cell proliferation.

Means for Attaining the Objects

The present inventors have conducted concentrated studies in order to attain the objects described above. As a result, they discovered that suppression of both GST-π and MRPL17 would more strongly induce cell death and more strongly suppress cell proliferation in cancer cells, compared with suppression of either GST-π or MRPL17. This has led to the completion of the present invention. The present invention includes the following.

(1) An agent for inducing cancer cell death comprising, as an active ingredient, a drug for suppressing GST-π and MRPL17 or comprising, as active ingredients, a drug for suppressing GST-π and a drug for suppressing MRPL17.

(2) An agent for suppressing cancer cell proliferation comprising, as an active ingredient, a drug for suppressing GST-π and MRPL17 or comprising, as active ingredients, a drug for suppressing GST-π and a drug for suppressing MRPL17.

(3) The agent according to (1) or (2), wherein the drug is a substance selected from the group consisting of an RNAi molecule, a ribozyme, an antisense nucleic acid, a DNA/RNA chimeric polynucleotide, and a vector expressing at least 1 of these substances.

(4) The agent according to (1) or (2), wherein the drug for suppressing MRPL17 is a compound that acts against the MRPL17.

(5) The agent according to (1), which induces apoptosis.

(6) The agent according to (1) or (2), wherein the cancer cell shows high-level expression of GST-π.

(7) A pharmaceutical composition used for treatment of a disease resulting from abnormal cell proliferation comprising the agent according to any of (1) to (6).

(8) A pharmaceutical composition used for treatment of a disease resulting from abnormal cell proliferation comprising, as an active ingredient, a drug for suppressing MRPL17, which is administered in combination with a drug for suppressing GST-π.

(9) A pharmaceutical composition used for treatment of a disease resulting from abnormal cell proliferation comprising, as an active ingredient, a drug for suppressing GST-π, which is administered in combination with a drug for suppressing MRPL17.

(10) The pharmaceutical composition according to any of (7) to (9), wherein the disease is cancer.

(11) The pharmaceutical composition according to (10), wherein the cancer shows high-level expression of GST-π.

(12) A method for screening for an agent for inducing cancer cell death and/or an agent for suppressing cancer cell proliferation used in combination with a drug for suppressing GST-π comprising selecting a drug for suppressing MRPL17.

(13) The method for screening according to (12) comprising steps of: bringing a test object into contact with a cancer cell; assaying the MRPL17 expression level in the cell; and selecting the test object as a drug for suppressing MRPL17 when the expression level is lower than the expression level assayed in the absence of the test object.

(14) A method for screening for an agent for inducing cancer cell death and/or an agent for suppressing cancer cell proliferation used in combination with a drug for suppressing MRPL17 comprising selecting a drug for suppressing GST-π.

(15) The method for screening according to (14) comprising steps of: bringing a test object into contact with a cancer cell; assaying the GST-π expression level in the cell; and selecting the test object as a drug for suppressing GST-π when the expression level is lower than the expression level assayed in the absence of the test object.

(16) A method for screening for an agent for inducing cell death and/or an agent for suppressing cell proliferation comprising selecting a drug for suppressing GST-π and MRPL17.

(17) The method for screening according to (16) comprising steps of: bringing a test object into contact with a cancer cell; assaying the GST-π expression level and the MRPL17 expression level in the cell; and selecting the test object as a drug for suppressing GST-π and MRPL17 when both the GST-π expression level and the MRPL17 expression level are lower than the expression level assayed in the absence of the test object.

This description includes part or all of the content as disclosed in the description and/or drawings of Japanese Patent Application No. 2016-124252, which is a priority document of the present application.

Effects of the Invention

The agent for inducing cell death according to the present invention can induce cancer cell death very strongly. Accordingly, the agent for inducing cell death according to the present invention can exert very high drug efficacy in the form of a pharmaceutical composition used for treatment of a disease resulting from abnormal cancer cell proliferation.

Also, the agent for suppressing cell proliferation according to the present invention can suppress cancer cell proliferation very strongly. Accordingly, the agent for suppressing cell proliferation according to the present invention can exert very high drug efficacy in the form of a pharmaceutical composition used for treatment of a disease resulting from abnormal cancer cell proliferation.

According to the method for screening of the present invention, in addition, an agent that induces cancer cell death and/or suppresses cancer cell proliferation very strongly can be selected.

BRIEF DESCRIPTION OF THE DRAWINGS

FIG. 1 shows a characteristic diagram showing the results of comparison of relative viability in cells expressing mutant KRAS when siRNA that suppresses GST-π expression and/or siRNA that suppresses MRPL17 expression are(is) allowed to act on the cells.

EMBODIMENTS FOR CARRYING OUT THE INVENTION

The agent for inducing cell death and the agent for suppressing cell proliferation according to the present invention comprise, as an active ingredient, a drug for suppressing GST-π and MRPL17 or comprise, as active ingredients, a drug for suppressing GST-π and a drug for suppressing MRPL17. The agent for inducing cell death and the agent for suppressing cell proliferation according to the present invention exert effects of inducing cancer cell death and effects of suppressing cancer cell proliferation. The term "cancer cell" used herein refers to a cell exhibiting abnormal proliferation caused by a gene (a cancer-associated gene).

Among cancer-associated genes, examples of cancer cells include KRAS genes, FOS genes, MYC genes, BCL-2 genes, and SIS genes. Among cancer-associated genes, examples of cancer suppressor genes include RB genes, p53 genes, BRCA1 genes, NF1 genes, and p73 genes. It should be noted that cancer cells are not limited to cancer cells associated with such particular cancer-associated genes, and examples of cancer cells encompasses an extensive range of cells exhibiting abnormal cell proliferation.

It is particularly preferable that the agent for inducing cell death and the agent for suppressing cell proliferation according to the present invention be applied to cancer cells showing high-level expression of GST-π. The term "cancer cells showing high-level expression of GST-π" refers to cells in which the GST-π expression level is significantly higher than that in normal cells among cells exhibiting abnormal cell proliferation (so-called cancer cells). The GST-π expression level can be assayed in accordance with a conventional technique, such as RT-PCR or microarray technology.

In many cases, an example of cancer cells showing high-level expression of GST-π is cancer cells expressing mutant KRAS. Specifically, it is preferable that the agent for inducing cell death and the agent for suppressing cell proliferation according to the present invention be applied to cancer cells expressing mutant KRAS.

The term "mutant KRAS" refers to a protein comprising an amino acid sequence derived from the amino acid sequence of wild-type KRAS via introduction of a mutation, such as deletion, substitution, addition, or insertion. A mutation of the mutant KRAS is so-called gain-of-function mutation. Specifically, mutant KRAS-expressing cells show, for example, lowered GTPase activity because of the mutation as described above, a GTP-bound active form is maintained, and signals directed toward the downstream are continuously maintained. As a result, abnormal cell proliferation takes place more frequently than in cells expressing wild-type KRAS. Examples of genes encoding the mutant KRAS include genes having a mutation in at least a site selected from among codon 12, codon 13, and codon 61 in the wild-type KRAS gene. It is particularly preferable that the mutant KRAS has mutations of codon 12 and codon 13. Specific examples include a mutation that substitutes glycine encoded by codon 12 of the KRAS gene with serine, aspartic acid, valine, cysteine, alanine, or arginine and a mutation that substitutes glycine encoded by codon 13 of the KRAS gene with aspartic acid.

The term "GST-π" used herein refers to an enzyme that catalyzes glutathione conjugation encoded by the GSTP1 gene. GST-π exists in a variety of animals including humans, and the sequence information thereof is also known (e.g., human: NM_000852 (NP_000843); rat: NM_012577 (NP_036709); and mouse: NM_013541 (NP_038569). The numbers indicate accession numbers of the NCBI database, the numbers outside the parentheses indicate nucleotide sequence numbers; and the numbers inside the parentheses indicate amino acid sequence numbers. For example, SEQ ID NO: 1 shows the nucleotide sequence of the coding region of the human GST-π gene registered in the database, and SEQ ID NO: 2 shows the amino acid sequence of the human GST-π protein encoded by the human GST-π gene.

MRPL17 is the mitochondrial ribosome protein L17 and is involved in protein synthesis in the mitochondria. The mitochondrial ribosome is composed of a small 28S subunit and a large 39S subunit. MRPL17 corresponds to the large 39S subunit.

MRPL17 exists in a variety of animals including humans, and the sequence information thereof is also known (e.g., human: NM_022061.3 (NP_071344.1)). The numbers indicate accession numbers of the NCBI database, the numbers outside the parentheses indicate nucleotide sequence numbers; and the numbers inside the parentheses indicate amino acid sequence numbers. For example, SEQ ID NO: 3 shows the nucleotide sequence of the human MRPL17 gene registered in the database under NM_022061.3, and SEQ ID NO: 4 shows the amino acid sequence of the human MRPL17 protein encoded by the human MRPL17 gene. It should be noted that MRPL17 is not limited to the protein comprising the amino acid sequence as shown in SEQ ID NO: 4 encoded by the nucleotide sequence as shown in SEQ ID NO: 3.

As described above, GST-π and MRPL17 can be identified on the basis of specific nucleotide sequences and amino acid sequences; however, a possibility of mutations occurring in nucleotide sequences and amino acid sequences among individual organisms (including the polymorphism) should be taken into consideration.

Specifically, GST-π and MRPL17 are not limited to proteins comprising the sequences identical to the amino acid sequences registered in the database. Proteins comprising sequences having at least 1 or 2, and typically at least 1 or several, such as 1, 2, 3, 4, 5, 6, 7, 8, 9, or 10 different amino acids from the sequence indicated above and having functions equivalent to those of GST-π and MRPL17 are within the scope of GST-π and MRPL17.

In addition, GST-π and MRPL17 encompass substances encoding proteins comprising nucleotide sequences exhibiting 70% or higher, 80% or higher, 90% or higher, 95% or higher, or 97% or higher identity to the particular nucleotide sequence indicated above and having functions equivalent to those of GST-π and MRPL17. Specific functions of GST-π and MRPL17 are as described above.

It should be noted that phrases such as "when used herein," "used herein," "in the present specification," and "described herein" mean, unless otherwise specified, that the description following them applies to all of the inventions described in the present specification. Further, unless otherwise defined, all of the technical terms and scientific terms used herein have the same meaning as that usually understood by a person skilled in the art. The entireties of all of the patents, patent publications, and other publications referred to herein are incorporated herein by reference.

The term "a drug for suppressing GST-π" used herein encompasses a drug for suppressing GST-π production and/or activity and an agent for promoting GST-π degradation and/or inactivation, and such drugs are not limited to these examples. Examples of drugs for suppressing GST-π production include, but are not limited to, an RNAi molecule, a ribozyme, an antisense nucleic acid, and a DNA/RNA chimeric polynucleotide for DNA encoding GST-π, and a vector expressing the same.

As a drug for suppressing GST-π, any compound that acts against GST-π can be used. Examples of compounds that can be used include organic compounds, such as amino acids, polypeptides or derivatives thereof, low-molecular-weight compounds, sugar, and polymeric compounds, and inorganic compounds. Such compounds may be natural substances or non-natural substances. Examples of polypeptide derivatives include modified polypeptides obtained with the addition of a modifying group and variant polypeptides obtained by modification of amino acid residues. In addition, a simple compound may be used. Alternatively, expression products of compound libraries and gene libraries, cell extracts, cull culture supernatants, products of fermentative microbes, extracts of marine organisms, or plant extracts may be used. Specifically, "the drug for suppressing GST-π" is not limited to a nucleic acid such as an RNAi molecule, and any compounds are within the scope of such drug.

Specific examples of drugs for suppressing GST-π activity include, but are not limited to, a substance that binds to GST-π, such as glutathione, a glutathione analog (e.g., glutathione analogs described in WO 95/08563, WO 96/40205, WO 99/54346, and Non-Patent Document 4), ketoprofen (Non-Patent Document 2), indomethacin (Hall et al., Cancer Res., 1989; 49 (22): 6265-8), ethacrynic acid, Piloprost (Tew et al., Cancer Res., 1988; 48 (13): 3622-5), an anti-GST-π antibody, and a GST-π dominant negative mutant. These drugs are either commercially available or may be produced appropriately based on known techniques.

The drug for suppressing GST-π production or activity is preferably an RNAi molecule, a ribozyme, an antisense nucleic acid, or a DNA/RNA chimeric polynucleotide for DNA encoding GST-π, or a vector expressing the same, in terms of high specificity and a low risk of side effects.

GST-π suppression may be determined based on whether or not GST-π expression or activity is more suppressed in cells, compared with a case in which a drug for suppressing GST-π is not utilized. GST-π expression may be evaluated by any known technique without limitation. Examples of such techniques include an immunoprecipitation method utilizing an anti-GST-π antibody, EIA, ELISA, IRA, IRMA, Western blotting, an immunohistochemical method, an immunocytochemical method, flow cytometry, various hybridization methods utilizing a nucleic acid that specifically hybridizes to a nucleic acid encoding GST-π or a unique fragment thereof or a transcription product (e.g., mRNA) or splicing product of such nucleic acid, Northern blotting, Southern blotting, and various PCR methods.

Further, GST-π activity may be evaluated by analyzing known GST-π activity including, but not limited to, activity of binding to a protein, such as Raf-1 (in particular, phosphorylated Raf-1) or EGFR (in particular, phosphorylated EGFR) by means of any known method such as immunoprecipitation, Western blotting, mass analysis, a pull-down method, or a surface plasmon resonance (SPR) method.

Examples of "the drug for suppressing MRPL17" used herein include, but are not limited to, a drug for suppressing MRPL17 production and/or activity and an agent for promoting MRPL17 degradation and/or inactivation. Examples of the drug for suppressing MRPL17 production include, but are not limited to, an RNA molecule, a ribozyme, an antisense nucleic acid, and a DNA/RNA chimeric polynucleotide for DNA encoding MRPL17, and a vector expressing the same. As a drug for suppressing MRPL17 activity and an agent for promoting MRPL17 degradation and/or inactivation, any compounds that act against MRPL17 can be used. Examples of compounds that can be used include organic compounds, such as amino acids, polypeptides or derivatives thereof, low-molecular-weight compounds, sugar, and polymeric compounds, and inorganic compounds. Such compounds may be natural substances or non-natural substances. Examples of polypeptide derivatives include modified polypeptides obtained with the addition of a modifying group and variant polypeptides obtained by modification of amino acid residues. In addition, a simple compound may be used. Alternatively, expression products of compound libraries and gene libraries, cell extracts, cull culture supernatants, products of fermentative microbes, extracts of marine organisms, or plant extracts may be used. Specifically, "the drug for suppressing MRPL17" is not limited to a nucleic acid such as an RNAi molecule, and any compounds are within the scope of such drug.

More specific examples of drugs for suppressing MRPL17 activity include, but are not limited to, an RNAi molecule, a ribozyme, an antisense nucleic acid, and a DNA/RNA chimeric polynucleotide for DNA encoding MRPL17, a vector expressing the same, an anti-MRPL17 antibody, and a MRPL17 dominant negative mutant. These drugs are either commercially available or may be produced appropriately based on known techniques.

In particular, the drug for suppressing MRPL17 production or activity is preferably an RNAi molecule, a ribozyme, an antisense nucleic acid, or a DNA/RNA chimeric polynucleotide for DNA encoding MRPL17, or a vector expressing the same, in terms of high specificity and a low risk of side effects.

MRPL17 suppression may be determined based on whether or not MRPL17 expression or activity is more suppressed in cells, compared with a case in which a drug for suppressing MRPL17 is not utilized. MRPL17 expression may be evaluated by any known technique without limitation. Examples of such techniques include an immunoprecipitation method utilizing an antibody, EIA, ELISA, IRA, IRMA, Western blotting, an immunohistochemical method, an immunocytochemical method, flow cytometry, various hybridization methods utilizing a nucleic acid that specifically hybridizes to a nucleic acid encoding the protein or a unique fragment thereof or a transcription product (e.g., mRNA) or splicing product of such nucleic acid, Northern blotting, Southern blotting, and various PCR methods.

Further, MRPL17 activity may be evaluated by analyzing known MRPL17 activity including, but not limited to, activity of binding to a small 28S subunit constituting the mitochondrial ribosome by means of any known method such as immunoprecipitation, Western blotting, mass analysis, a pull-down method, or a surface plasmon resonance (SPR) method.

Examples of "the drug for suppressing GST-π and MRPL17" used herein include, but are not limited to, an agent for suppressing both GST-π production and/or activity and MRPL17 production and/or activity and an agent for promoting both GST-π degradation and/or inactivation and MRPL17 degradation and/or inactivation. Examples of the drug for suppressing GST-π and MRPL17 production include, but are not limited to, an RNAi molecule, a ribozyme, an antisense nucleic acid, and a DNA/RNA chimeric polynucleotide for DNA encoding GST-π and DNA encoding MRPL17, and a vector expressing the same. As a drug for suppressing GST-π and MRPL17 activity and an agent for promoting GST-π and MRPL17 degradation and/or inactivation, any compounds that act against GST-π and MRPL17 can be used. Examples of compounds that can be used include organic compounds, such as amino acids, polypeptides or derivatives thereof, low-molecular-weight compounds, sugar, and polymeric compounds, and inorganic compounds. Such compounds may be natural substances or non-natural substances. Examples of polypeptide derivatives include modified polypeptides obtained with the addition of a modifying group and variant polypeptides obtained by modification of amino acid residues. In addition, a simple compound may be used. Alternatively, expression products of compound libraries and gene libraries, cell extracts, cull culture supernatants, products of fermentative microbes, extracts of marine organisms, or plant extracts may be used. Specifically, "the drug for suppressing GST-π and MRPL17" is not limited to a nucleic acid such as an RNAi molecule, and any compounds are within the scope of such drug.

When used herein, the RNAi molecule denotes any molecule that causes RNA interference, including, but not limited to, a double-stranded RNA such as siRNA (small interfering RNA), miRNA (micro RNA), shRNA (short hairpin RNA), ddRNA (DNA-directed RNA), piRNA (Piwi-interacting RNA), or rasiRNA (repeat associated siRNA), and modified forms thereof. These RNAi molecules may be commercially available or may be designed and prepared based on known sequence information; i.e., the nucleotide sequences and/or the amino acid sequences as shown in SEQ ID NOs: 1 to 4.

When used herein, the antisense nucleic acid includes RNA, DNA, PNA, and a complex thereof.

When used herein, the DNA/RNA chimeric polynucleotide includes, but is not limited to, a double-stranded polynucleotide composed of DNA and RNA that inhibits the expression of a target gene described in, for example, JP 2003-219893 A.

The drug for suppressing GST-π and the drug for suppressing MRPL17 may be contained in a single formulation or may be contained separately in 2 or more formulations. In the case of the latter, each formulation may be administered at the same time or they may be administered with a time interval therebetween. When administered with a time interval therebetween, the formulation containing a drug for suppressing GST-π may be administered before or after the formulation containing a drug for suppressing MRPL17 is administered.

When MRPL17 is suppressed together with GST-π, it shows synthetic lethality in cancer cells. Accordingly, the drug for suppressing MRPL17 can serve as an active ingredient of an agent or composition for inducing cell death and/or for potentiating cell proliferation suppression by the drug for suppressing GST-π (hereafter, also referred to as an "agent for enhancing cell death induction," "agent for enhancing cell proliferation suppression," "composition for enhancing cell death induction," or "composition for enhancing cell proliferation suppression"). In other words, administration of effective amount of the drug for suppressing MRPL17 can enhance induction of cell death and/or suppression of cell proliferation caused by administration of the drug for suppressing GST-π.

The term "synthetic lethality" used herein refers to a phenomenon, such that deletion of a single gene shows no or low lethality to a cell or organism but deletion of a plurality of genes shows lethality or significantly high lethality. In particular, the term "synthetic lethality" used herein refers to lethality to cancer cells.

The amount of active ingredients to be incorporated into the agent or composition of the present invention may be an amount that induces cell death such as apoptosis and/or suppresses cell proliferation in cells to which the agent or composition is administered. An amount that does not cause an adverse effect that exceeds the benefit of administration is preferable. Such an amount is known or may be determined appropriately by an in vitro test using cultured cells and the like or a test in a model animal such as a mouse, a rat, a dog, or a pig, and such test method is well known to a person skilled in the art. Induction of apoptosis may be evaluated by various known techniques, such as detection of an apoptosis-specific phenomenon such as DNA fragmentation, binding of annexin V to cell membrane, change in mitochondrial membrane potential, or activation of caspase, or by TUNEL staining. Further, suppression of cell proliferation may be evaluated by various known methods, for example, counting of the number of living cells over time, measurement of the size, volume, or weight of a tumor, measurement of the amount of DNA synthesized, the WST-1 method, the Braj (bromodeoxyuridine) method, or the $^3$H thymidine incorporation method. The amount of active ingredient incorporated can vary according to the manner in which the agent or composition is administered. When a plurality of units of the composition is used for 1 administration, for example, the amount of active ingredient to be incorporated in 1 unit of the composition may be determined by dividing the amount of active ingredient necessary for 1 administration by the plurality of units. A person skilled in the art can adequately adjust such amount.

By incorporating the drug for suppressing GST-π and the drug for suppressing MRPL17 as active ingredients, the agent for inducing cell death, the agent for suppressing cell proliferation, the composition for inducing cell death, or the composition for suppressing cell proliferation can be produced.

The present invention can further provide a combination of the drug for suppressing GST-π and the drug for suppressing MRPL17 used for induction of cell death or suppression of cell proliferation. In addition, the present invention provides a method for inducing cell death or a method for suppressing cell proliferation comprising administering effective amount of the drug for suppressing GST-π and the drug for suppressing MRPL17.

All of the above methods for inducing cell death such as apoptosis or suppressing cell proliferation may be either an in vitro method or an in vivo method. Further, the agent used in the method is as described above, and the effective amount of the agent may be an amount that induces cell death or suppresses cell proliferation in cells to which the agent is administered. An amount that does not cause an adverse effect that exceeds the benefit of administration is preferable. Such an amount is known or may be determined appropriately by an in vitro test using cultured cells and the like, and such test method is well known to a person skilled in the art. Induction of cell death or suppression of cell proliferation may be evaluated by various known techniques, including those described above. The effective amount is not necessarily one that causes cell death or proliferation suppression in all the cells of a cell population to which the agent is administered. For example, the effective amount may be an amount that causes cell death or proliferation suppression in at least 1%, at least 2%, at least 3%, at least 4%, at least 5%, at least 6%, at least 8%, at least 10%, at least 12%, at least 15%, at least 20%, or at least 25% of the cells of the cell population.

The agent for inducing cell death or the agent for suppressing cell proliferation according to the present invention can effectively induce cancer cell death or suppress cancer cell proliferation. Thus, such agent is effective as an ingredient of a pharmaceutical composition used for treatment of a disease resulting from abnormal cell proliferation. By incorporating the drug for suppressing GST-π and the drug for suppressing MRPL17 as active ingredients, in addition, a pharmaceutical composition used for treatment of a disease resulting from abnormal cell proliferation can be produced. Further, a disease resulting from abnormal cell proliferation can be treated via administration of an effective amount of the pharmaceutical composition to a target who is in need of treatment.

The pharmaceutical composition is effective for treatment of a disease resulting from abnormal cell proliferation and it is particularly effective for treatment of a disease resulting from cell death or abnormal cell proliferation caused by mutant KRAS expression.

Examples of diseases caused by mutant KRAS-expressing cells include, but are not limited to, a benign or malignant tumor (also referred to as cancer or malignant neoplasm), hyperplasia, keloid, Cushing's syndrome, primary aldosteronism, erythroplakia, polycythemia vera, leukoplakia, hyperplastic scar, lichen planus, and lentiginosis.

Examples of the cancer in the present invention include cancer, cancer exhibiting high-level expression of GST-π and cancer caused by cells showing mutant KRAS expression, which may be simply referred to as "KRAS cancer." KRAS cancer is often within the scope of cancer exhibiting high-level expression of GST-π. Examples of the cancer in the present invention include, but are not limited to, sarcomas such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, and osteosarcoma, carcinomas such as brain tumor, head and neck carcinoma, breast carcinoma, lung carcinoma, esophageal carcinoma, gastric carcinoma, duodenal carcinoma, appendiceal carcinoma, colon carcinoma, rectal carcinoma, liver carcinoma, pancreatic carcinoma, gall bladder carcinoma, bile duct carcinoma, anal carcinoma, renal carcinoma, ureteral carcinoma, bladder carcinoma, prostate carcinoma, penile carcinoma, testicular carcinoma, uterine carcinoma, ovarian carcinoma, vulva carcinoma, vaginal carcinoma, and skin carcinoma, and, furthermore, leukemia and malignant lymphoma. In the present invention, "cancer" includes epithelial malignancy and non-epithelial malignancy. The cancer in the present invention can be present at any site of the body, for example, the brain, head and neck, chest, limbs, lung, heart, thymus, esophagus, stomach, small intestine (duodenum, jejunum, ileum), large intestine (colon, cecum, appendix, rectum), liver, pancreas, gallbladder, anus, kidney, urinary duct, bladder, prostate, penis, testis, uterus, ovary, vulva, vagina, skin, striated muscle, smooth muscle, synovial membrane, cartilage, bone, thyroid, adrenal gland, peritoneum, mesentery, bone marrow, blood, vascular system, lymphatic system such as lymph node, or lymphatic fluid.

The pharmaceutical composition may be used in combination with active ingredients other than the drug for suppressing GST-π and the drug for suppressing MRPL17. When the pharmaceutical composition is used in combination herein, for example, another active ingredient is administered as a separate formulation, and another active ingredient is administered in the form of a mixture with at least 1 type of other medicinal agent. When administered as a separate formulation, a formulation containing another active ingredient may be administered prior to, at the same time as, or subsequent to another formulation.

An example of other active ingredient is a substance that is effective in treatment of a target disease. When a disease to be treated is cancer, for example, an anticancer agent may be used in combination. Examples of anticancer agents include: alkylating agents, such as ifosfamide, nimustine hydrochloride, cyclophosphamide, dacarbazine, melphalan, and ranimustine; metabolism antagonists, such as genicitabine hydrochloride, enocitabine, cytarabine ocfosfate, a cytarabine formulation, a tegafur/uracil or tegafur/gimeracil/oteracil potassium combination drug (e.g., TS-1), doxifluridine, hydroxycarbamide, fluorouracil, methotrexate, and mercaptopurine; antitumor antibiotics, such as idarubicin hydrochloride, epirubicin hydrochloride, daunorubicin hydrochloride, daunorubicin citrate, doxorubicin hydrochloride, pirarubicin hydrochloride, bleomycin hydrochloride, peplomycin sulfate, mitoxantrone hydrochloride, and mitomycin C; alkaloids, such as etoposide, irinotecan hydrochloride, vinorelbine tartarate, docetaxel hydrate, paclitaxel, vincristine sulfate, vindesine sulfate, and vinblastine sulfate; hormonal therapeutic agents, such as anastrozole, tamoxifen citrate, toremifene citrate, bicalutamide, flutamide, and estramustine phosphorate; platinum complexes, such as carboplatin, cisplatin (CDDP), and nedaplatin; angiogenesis inhibitors, such as thalidomide, neovastat, and bevacizumab; and L-asparaginase.

When the active ingredient used in the various agents or compositions and treatment methods of the present invention described herein is a nucleic acid, such as an RNAi molecule, a ribozyme, an antisense nucleic acid, or a DNA/RNA chimeric polynucleotide, for example, it may be used as a naked nucleic acid as it is, but it may also be carried by various vectors. As the vector, any known vector such as a plasmid vector, a phage vector, a phagemid vector, a cosmid vector, or a virus vector may be used. The vector preferably contains at least a promoter that enhances expression of the nucleic acid carried, and, in this case, the nucleic acid is preferably operably linked to such a promoter. When the nucleic acid is operably linked to a promoter herein, the nucleic acid and the promoter are positioned so that a protein encoded by the nucleic acid is appropriately produced by the action of the promoter. The vector may or may not be replicable in a host cell, and the transcription of a gene may be carried out either outside or inside the nucleus of a host cell. In the case of the latter, the nucleic acid may be incorporated into the genome of a host cell.

Further, the active ingredient may be carried by various non-viral lipid or protein carriers. Examples of such carriers include, but are not limited to, cholesterol, a liposome, an antibody protomer, cyclodextrin nanoparticles, a fusion peptide, an aptamer, a biodegradable polylactic acid copolymer, and a polymer, and the efficiency of incorporation into cells can be enhanced (see, e.g., Pirollo and Chang, Cancer Res., 2008; 68 (5): 1247-50). In particular, a cationic liposome or a polymer (e.g., polyethylenimine) is useful. Further examples of useful polymers as such a carrier include those described in, for example, US 2008/0207553 or US 2008/0312174.

With regard to the various pharmaceutical compositions of the present invention described herein, the active ingredient may be combined with another optional ingredient as long as the effect of the active ingredient is not impaired. Examples of such an optional ingredient include another chemical therapeutic agent, a pharmacologically acceptable carrier, an excipient, and a diluent. In accordance with the route of administration, the mode of drug release, and other conditions, the composition may be coated with an appropriate material such as an enteric coating or a timed disintegration material, or it may be incorporated into an appropriate drug release system.

The various agents and compositions (including the various pharmaceutical compositions) of the present invention described herein may be administered via various routes including both oral and parenteral routes. Examples thereof include, but are not limited to, oral, intravenous, intramuscular, subcutaneous, local, intratumoral, rectal, intraarterial, intraportal, intraventricular, transmucosal, transdermal, intranasal, intraperitoneal, intrapulmonary, and intrauterine routes. Such agents and compositions may be formulated into a dosage form suitable for each administration route.

With regard to the dosage forms and formulation methods, any known forms or methods may be employed appropriately (see, for example, Hyojun yakuzaigaku (Standard Pharmaceutical Science), Yoshiteru Watanabe et al. (ed.), Nankodo, 2003).

Examples of the dosage forms suitable for oral administration include, but are not limited to, a powder, granules, a tablet, a capsule, a liquid, a suspension, an emulsion, a gel, and a syrup, and examples of the dosage forms suitable for parenteral administration include an injection such as a solution injection, a suspension injection, an emulsion injection, and an injection in a form that is prepared at the time of use. A formulation for parenteral administration may be in the form of an aqueous or nonaqueous isotonic sterile solution or suspension.

The various agents or compositions (including various pharmaceutical compositions) of the present invention described herein may be targeted to specific tissue or cells. Targeting may be achieved by any known technique. When delivery to a cancer is attempted, for example, a technique such as passive targeting in which a formulation is made into a size of 50 to 200 μm, and, in particular, 75 to 150 μm in diameter, which is suitable for exhibition of an enhanced permeability and retention (EPR) effect, or active targeting in which a ligand of CD19, HER2, a transferrin receptor, a folic acid receptor, a VIP receptor, EGFR (Torchilin, AAPS J. 2007; 9 (2): E128-47), RAAG10 (JP 2005-532050 A), PIPA (JP 2006-506071 A), or KID3 (JP 2007-529197 A), a peptide having an RGD motif or an NGR motif, F3, LyP-1 (Ruoslahti et al., J. Cell Biol., 2010; 188(6): 759-68) is used as a targeting agent may be employed, although the technique is not limited thereto. Since a retinoid or a derivative thereof is known to be useful as a targeting agent for cancer cells (WO 2008/120815), a carrier containing a retinoid as a targeting agent may also be used. Such carriers are described in, for example, WO 2009/036368, WO 2010/014117, and WO 2012/170952, in addition to the literature mentioned above.

The various agents or compositions (including various pharmaceutical compositions) of the present invention described herein may be supplied in any form. From the viewpoint of storage stability, such agents or compositions may be provided in a form that can be prepared at the time of use, such as a form that allows a doctor and/or pharmacist, a nurse, or other paramedic to prepare it at the medical site or in the vicinity thereof. Such a form is particularly useful when the agent or composition of the present invention contains a component that is difficult to store stably, such as a lipid, a protein, or a nucleic acid. In such a case, the agent or composition of the present invention is provided in 1 or more containers containing at least 1 of the essential constituents, and it is prepared prior to use, for example, within 24 hours, preferably within 3 hours, and more preferably immediately before use. At the time of preparation, a reagent, a solvent, preparation equipment, etc., that are usually available at a place of preparation may be used according to need.

Therefore, the present invention also relates to a kit for preparing a composition comprising 1 or more containers containing active ingredients to be incorporated into the various agents or compositions of the present invention alone or in combination and essential constituents of the various agents or compositions provided in the form of such kit. The kit of the present invention may include, in addition to the above, instructions such as a written explanation or an electronic recording medium such as a CD or DVD describing a preparation method, an administration method, etc., for the various agents or compositions of the present invention. Further, the kit of the present invention may contain all of the constituents for completing the various agents or compositions of the present invention, but it may not necessarily contain all of the constituents. Therefore, the kit of the present invention may not need to contain a reagent or a solvent that is usually available at a medical site, an experimental laboratory, etc., such as sterile water, physiological saline, or a glucose solution.

The effective amount in the various treatment methods of the present invention described herein is, for example, an amount that reduces symptoms of a disease or delays or stops the progress of a disease, and it is preferably an amount that suppresses or cures a disease. An amount that does not cause an adverse effect that exceeds the benefit of administration is preferable. Such an amount may be determined appropriately by an in vitro test using cultured cells and the like, or a test in a model animal such as a mouse, a rat, a dog, or a pig, and such test methods are well known to a person skilled in the art. Further, the dose of a drug used in the treatment method of the present invention is known to a person skilled in the art or may be determined appropriately by the tests described above.

The specific dose of the active ingredient to be administered in the treatment method of the present invention described herein can be determined by taking various conditions related to the subject that requires treatment, such as the severity of symptoms, the general health state, the age, the body weight, and the gender of the subject, diet, the timing and frequency of administration, concomitant pharmaceuticals, the responsiveness to the treatment, the dosage form, and compliance with the treatment, into consideration.

Examples of administration routes include various routes, including both oral and parenteral routes, such as oral, intravenous, intramuscular, subcutaneous, local, intratumoral, rectal, intraarterial, intraportal, intraventricular, transmucosal, transdermal, intranasal, intraperitoneal, intrapulmonary, and intrauterine routes.

The frequency of administration depends on the properties of the agent or composition used and the condition of the subject, including those described above, and it may be a plurality of times a day (that is, 2, 3, 4, 5, or more times a day), once a day, every few days (that is, every 2, 3, 4, 5, 6, 7 days, etc.), every week, or every few weeks (that is, every 2, 3, 4 weeks, etc.).

When used herein, the term "subject" means any biological individual and is preferably an animal, more preferably a mammal, and further preferably a human individual. In the present invention, the subject may be healthy or affected by some disease. When treatment of a specific disease is intended, typically, a subject is affected by such disease or is at a risk of affection.

The term "treatment" used herein encompasses all types of preventive and/or therapeutic interventions medically allowed for the purpose of, for example, cure, temporary remission, or prevention of a disease. For example, the term "treatment" encompasses medically allowable interventions for various types of purposes, such as delay or suppression the disease progress, regression or disappearance of a lesion, prevention of the onset, or inhibition of recurrence.

MRPL17 is a protein showing synthetic lethality in cancer cells when it is suppressed together with GST-π, as described above. With the use of suppression of MRPL17 as the indicator, accordingly, an agent for inducing cancer cell death and/or an agent for suppressing cancer cell proliferation used in combination with the drug for suppressing GST-π can be screened for. Specifically, a substance that can suppress MRPL17 can be a candidate substance for the agent for inducing cancer cell death and/or the agent for suppressing cancer cell proliferation used in combination with the drug for suppressing GST-π.

For example, a test object is brought into contact with a cancer cell, such as a cell that expresses mutant KRAS, and the expression level of MRPL17 that shows synthetic lethality in the cell that expresses mutant KRAS upon suppression thereof together with GST-π is assayed in the cell. When the expression level assayed upon contact with the test object is lower than the expression level assayed in the absence of the test object, such test object can be selected as a candidate substance for the drug for suppressing MRPL17.

The drug for suppressing GST-π is a protein showing synthetic lethality in cancer cells when it is suppressed together with the drug for suppressing MRPL17. With the use of suppression of GST-π as the indicator, accordingly, an agent for inducing cancer cell death and/or an agent for suppressing cancer cell proliferation used in combination with the drug for suppressing MRPL17 can be screened for. Specifically, a substance that can suppress GST-π can be a candidate substance for the agent for inducing cancer cell death and/or the agent for suppressing cancer cell proliferation used in combination with the drug for suppressing MRPL17.

For example, a test object is brought into contact with a cancer cell, such as a cell that expresses mutant KRAS, and the expression level of GST-π is assayed in the cell. When the expression level assayed upon contact with the test object is lower than the expression level assayed in the absence of the test object, such test object can be selected as a candidate substance for the drug for suppressing GST-π.

With the use of suppression of GST-π and suppression of MRPL17 as indicators, also, an agent for inducing cancer cell death and/or an agent for suppressing cancer cell proliferation can be screened for. Specifically, a substance that can suppress GST-π and MRPL17 can be a candidate substance for the agent for inducing cancer cell death and/or the agent for suppressing cancer cell proliferation.

For example, a test object is brought into contact with a cancer cell, such as a cell that expresses mutant KRAS, and the expression level of GST-π and that of MRPL17 are assayed in the cell. When the expression levels assayed upon contact with the test object are lower than the expression levels assayed in the absence of the test object, such test object can be selected as a candidate substance for the drug for suppressing GST-π and MRPL17.

Any substance may be used as a test substance without particular limitation. A simple substance may be used, or a mixture of a plurality of constituents may be used. For example, a test substance may contain an unidentified substance such as an extract from microorganisms or a culture solution, or a test substance may comprise known compositions at a given proportion. A test substance may be any of a protein, nucleic acid, lipid, polysaccharide, organic compound, or inorganic compound.

EXAMPLES

Hereafter, the present invention is described in greater detail with reference to the examples, although the technical scope of the present invention is not limited to the examples below.

[Experiment] Knockdown of GST-π and MRPL17 by siRNA

As the example of cancer cells, $0.5 \times 10^5$ A549 cells (human lung cancer cells with KRAS mutation) were sowed in a 6-cm petri dish and then cultured in the Dulbecco's modified Eagle's medium (DMEM, Sigma) supplemented with 10% fetal bovine serum (FBS), 1% L-glutamine, and 1% L-glutamine-penicillin streptomycin (Sigma) for 18 hours. Culture was conducted at 37° C. in the presence of 5% $CO_2$ unless otherwise specified.

In this experiment, at the outset, 20% to 30% confluent A549 cells were transfected with GST-π siRNA and/or MRPL17 siRNA using Lipofectamine RNAiMAX (Life Technologies) in the manner described below.

A lipofectamine/siRNA mixed solution for transfection was prepared as follows. First, 6 μl of lipofectamine RNAiMAX and 244 μl of OPTI-MEM (Sigma) were mixed to prepare a lipofectamine solution. Subsequently, a predetermined amount of 50 μM siRNA was diluted to 250 ml with OPTI-MEM to prepare an siRNA solution (when preparing a siRNA solution having a final concentration of 40 nM, for example, 4.4 μl of 50 μM siRNA and 245.6 μl of OPTI-MEM were mixed), and the resultant was mixed with the lipofectamine solution and allowed to stand at room temperature for 15 minutes. During this period, the medium was removed by suction from the 6-cm petri dish in which A549 cells were cultured and then replaced with 5 ml of Opti-MEM. The siRNA/lipofectamine mixed solution (500 μl) was added thereto. siRNAs indicated below were used. In the following, a capital letter indicates RNA and a small letter indicates DNA.

```
GST-π siRNA:
Sense strand:
                                        (SEQ ID NO: 5)
CCUUUUGAGACCCUGCUGUtt Antisense strand:
                                        (SEQ ID NO: 6)
ACAGCAGGGUCUCAAAAGGct MRPL17 siRNA:
Sense strand:
                                        (SEQ ID NO: 7)
UGGCAGUGAUCGAGUAUAAtt Antisense strand:
                                        (SEQ ID NO: 8)
UUAUACUCGAUCACUGCCAtt Control siRNA:
Sense strand:
                                        (SEQ ID NO: 9)
ACGUGACACGUUCGGAGAAtt Antisense strand:
                                        (SEQ ID NO: 10)
UUCUCCGAACGUGUCACGUtt
```

GST-π siRNA and MRPL17 siRNA at the final concentration of 1.25, 2.5, 5, 10, 20, or 40 nM and GST-π siRNA or MRPL17 siRNA at the final concentration of 1.25, 2.5, 5, 10, 20, or 40 nM (control siRNA was also added at the final concentration of 1.25, 2.5, 5, 10, 20, or 40 nM) were added to the petri dish containing A549 cells, and culture was conducted at 37° C. in the presence of 5% $CO_2$ for 5 hours. A control sample prepared with the addition of control siRNA at the final concentration of 2.5, 5, 10, 20, 40, or 80 nM was used. Opti-MEM was removed by suction from the petri dish 5 hours later, and the Dulbecco's modified Eagle's medium (DMEM, Sigma) supplemented with 10% fetal bovine serum (FBS), 1% L-glutamine, and 1% L-glutamine-penicillin streptomycin (Sigma) was added thereto. The medium was removed by suction from the petri dish 3 days later, the cell surface was washed with PBS, and cells adhered to the petri dish were peeled with the use of trypsin to prepare a cell suspension in DMEM. The resulting cell suspension was applied dropwise onto C-CHIP (Digital Bio), and the total cell count was determined based on the microscope image.

The results are shown in FIG. 1. As shown in FIG. 1, when GST-π siRNA is used in combination with MRPL17 siRNA at the total siRNA concentration of 40 nM or lower, A549 cell proliferation was more strongly inhibited compared with the case in which either GST-π siRNA or MRPL17 siRNA was used alone. Specifically, the results shown in FIG. 1 demonstrate that the effects of suppressing cancer cell proliferation achieved with the use of the drug for suppressing GST-π in combination with the drug for suppressing MRPL17 to cancer cells are superior to those achieved with the use of either one thereof.

All publications, patents, and patent applications cited herein are incorporated herein by reference in their entirety.

The invention claimed is:

1. A pharmaceutical agent comprising, as active ingredients, a first drug which suppresses expression of GST-π and a second drug which suppresses expression of MRPL17, wherein the first and second drugs are selected from the group consisting of an RNAi molecule, a ribozyme, an antisense nucleic acid, a DNA/RNA chimeric polynucleotide, and a vector expressing at least one of these substances,
    wherein the nucleotide sequence of GST-π has 90% or higher identity to SEQ ID NO: 1 and encodes a protein having functions equivalent to a protein having an amino acid sequence of SEQ ID NO: 2,
    wherein the nucleotide sequence of MRPL17 has 90% or higher identity to SEQ ID NO: 3 and encodes a protein having functions equivalent to a protein having an amino acid sequence of SEQ ID NO: 4.

2. The pharmaceutical agent according to claim 1, wherein the second drug which suppresses the expression of MRPL17 is a compound that inhibits MRPL17.

3. The pharmaceutical agent according to claim 1, wherein said pharmaceutical agent induces apoptosis.

4. A method for inhibiting a cancer resulting from abnormal cancer cell proliferation, the method comprising administering to a subject a first drug which suppresses expression of MRPL17 in combination with a second drug which suppresses expression of GST-π, wherein the first and second drugs are selected from the group consisting of an RNAi molecule, a ribozyme, an antisense nucleic acid, a DNA/RNA chimeric polynucleotide, and a vector expressing at least one of these substances, wherein the cancer cell has KRAS mutation,
    wherein the nucleotide sequence of GST-π has 90% or higher identity to SEQ ID NO: 1 and encodes a protein having functions equivalent to a protein having an amino acid sequence of SEQ ID NO: 2,
    wherein the nucleotide sequence of MRPL17 has 90% or higher identity to SEQ ID NO: 3 and encodes a protein having functions equivalent to a protein having an amino acid sequence of SEQ ID NO: 4.

5. The method of claim 4, wherein the cancer presents a high-level of expression of GST-π.

6. The pharmaceutical agent of claim 1, wherein the first drug which suppresses the expression of GST-π comprises a first siRNA, and the second drug which suppresses the expression of MRPL17 comprises a second siRNA.

7. The pharmaceutical agent of claim 6, wherein the first siRNA comprises a sense strand having a nucleic acid sequence in accordance with SEQ ID NO: 5, and an antisense strand having a nucleic acid sequence in accordance with SEQ ID NO: 6.

8. The pharmaceutical agent of claim 6, wherein the second siRNA comprises a sense strand having a nucleic acid sequence in accordance with SEQ ID NO: 7, and an antisense strand having a nucleic acid sequence in accordance with SEQ ID NO: 8.

9. The pharmaceutical agent of claim 6, wherein the first siRNA comprises a sense strand having a nucleic acid sequence in accordance with SEQ ID NO: 5, and an antisense strand having a nucleic acid sequence in accordance with SEQ ID NO: 6, and the second siRNA comprises a sense strand having a nucleic acid sequence in accordance with SEQ ID NO: 7, and an antisense strand having a nucleic acid sequence in accordance with SEQ ID NO: 8.

10. The method of claim 4, wherein the first drug which suppresses the expression of GST-π comprises a first siRNA, and the second drug which suppresses the expression of MRPL17 comprises a second siRNA.

11. The method of claim 10, wherein the first siRNA comprises a sense strand having a nucleic acid sequence in accordance with SEQ ID NO: 5, and an antisense strand having a nucleic acid sequence in accordance with SEQ ID NO: 6.

12. The method of claim 10, wherein the second siRNA comprises a sense strand having a nucleic acid sequence in accordance with SEQ ID NO: 7, and an antisense strand having a nucleic acid sequence in accordance with SEQ ID NO: 8.

13. The method of claim 10, wherein the first siRNA comprises a sense strand having a nucleic acid sequence in accordance with SEQ ID NO: 5, and an antisense strand having a nucleic acid sequence in accordance with SEQ ID NO: 6, and the second siRNA comprises a sense strand having a nucleic acid sequence in accordance with SEQ ID NO: 7, and an antisense strand having a nucleic acid sequence in accordance with SEQ ID NO: 8.

* * * * *